United States Patent [19]

Floyd, Jr.

[11] 4,076,732
[45] Feb. 28, 1978

[54] DERIVATIVES OF α-(6-CARBOXYHEXYL) FURFURYL ALCOHOL

[75] Inventor: Middleton Brawner Floyd, Jr., Suffern, N.Y.

[73] Assignee: American Cyanamid Company, Stamford, Conn.

[21] Appl. No.: 782,861

[22] Filed: Mar. 30, 1977

[51] Int. Cl.$^2$ .......................................... C07D 307/54
[52] U.S. Cl. ........................... 260/347.3; 260/514 D; 560/121
[58] Field of Search ................ 260/347.3, 347.4, 347.5

[56] References Cited

U.S. PATENT DOCUMENTS

| | | | |
|---|---|---|---|
| 3,952,033 | 4/1976 | Floyd | 260/347.5 X |
| 4,009,187 | 2/1977 | Eliasson et al. | 260/347.3 |
| 4,021,452 | 5/1977 | Floyd | 260/347.3 |

OTHER REFERENCES

Piancatelli et al., Tetrahedron Letters, No. 13 (1977), pp. 1131-1134.
King, Journal of the Chemical Society, 1938, pp. 1826-1828.

*Primary Examiner*—Richard L. Raymond
*Attorney, Agent, or Firm*—Denis A. Polyn

[57] ABSTRACT

This disclosure describes novel derivatives of α-(6-carboxyhexyl) furfuryl alcohol which are useful as intermediates for the preparation of natural prostaglandins and their congeners.

5 Claims, No Drawings

DERIVATIVES OF α-(6-CARBOXYHEXYL) FURFURYL ALCOHOL

BACKGROUND OF THE INVENTION

The novel compounds of structure VIII (infra) are useful precursors to the previously disclosed compounds of structure IX (infra), shown in U.S. Pat. No. 3,952,033, which are in turn precursors to the compounds of structure X which are also disclosed in the aforementioned patent. A process related to the one disclosed in the instant application is found in *Tetrahedron Letters* No. 39, pp. 3555–3558, 1976 (G. Piancatelli et al.).

SUMMARY OF THE INVENTION

This invention relates to novel compounds useful as intermediates for the synthesis of the natural prostaglandins and their congeners. These novel compounds may be represented by the following structural formula:

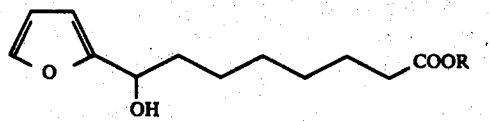

wherein R is selected from the group consisting of hydrogen and $C_1-C_6$ alkyl. The invention also relates to compounds of the formula:

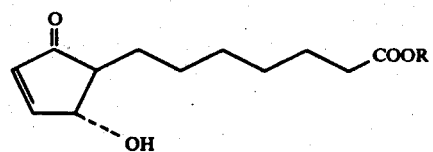

wherein R is as previously defined.

The formation of the novel furylcarbinol derivatives of this invention may be accomplished as illustrated in Flowsheet A, wherein R is as previously defined.

FLOWSHEET A

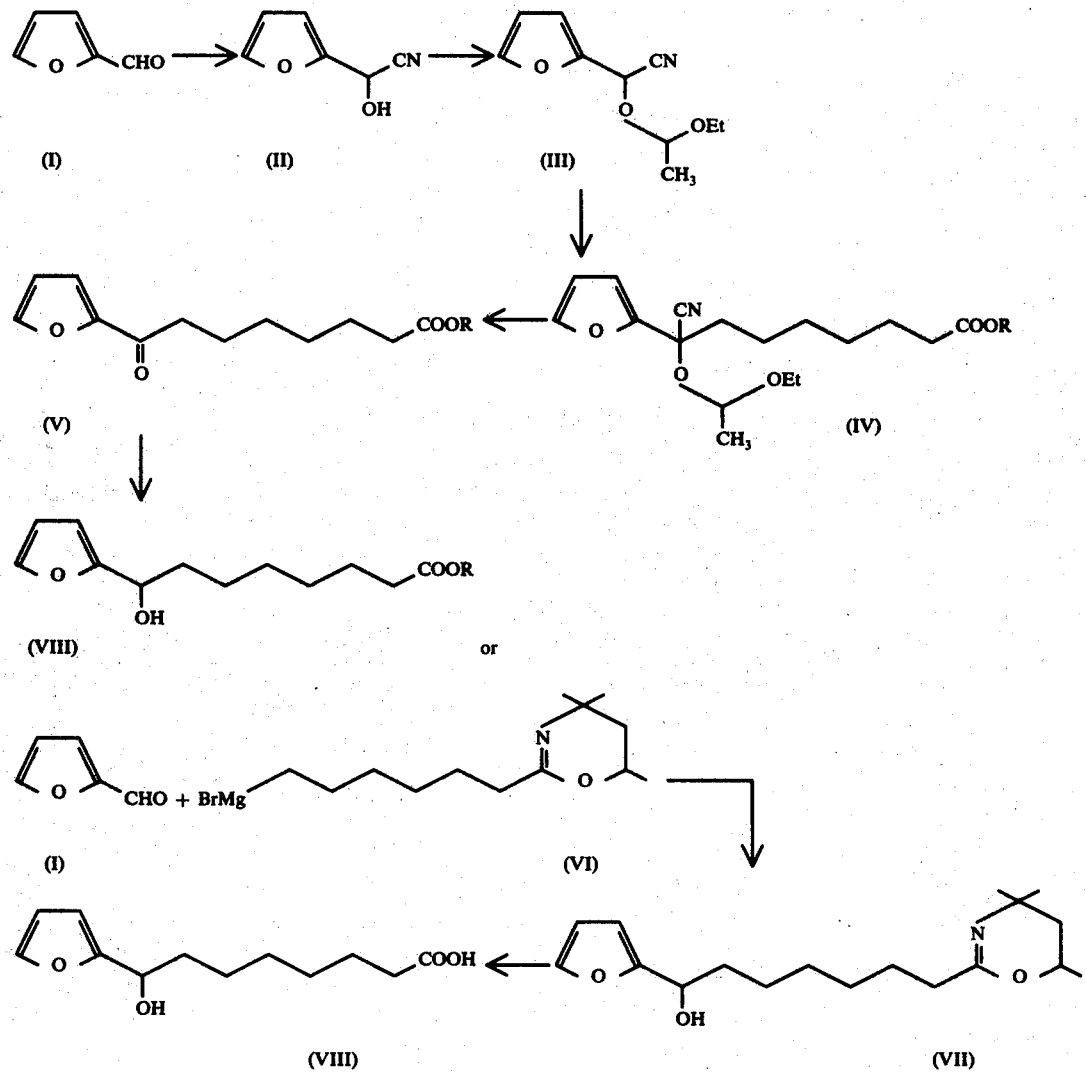

In accordance with the illustrative equations of Flowsheet A hereinabove, furfural cyanohydrin (II) is prepared from furfural (I) and reacted with ethyl vinyl ether in the presence of an acid catalyst, preferably dichloro-O-protected cyanohydrin may be converted to an anionic species by treatment with a very strong base, preferably lithium diisopropylamide in an inert solvent. The resulting species is treated with a 7-haloheptanoate ester in an alkylation reaction to provide the ester cyanohydrin ether IV. The preferred alkylating agent is ethyl 7-bromoheptanoate. The preferred solvent for the conversion is tetrahydrofuran. It is advantageous to employ a highly polar complexing agent in the alkylation phase of the reaction. For this purpose a 10-20% molar excess of hexamethylphosphoric triamide (HMPA) or N-methyl-2-pyrrolidone as a mixture with the ether III may be added to a mixture of the strong base and solvent at low temperature, preferably −78° to −50°. After a suitable period, for example 30 minutes at −78°, the mixture is treated with the alkylating agent dropwise. The resulting mixture is allowed to warm to room temperature slowly over a period of several hours. The principle involved in the alkylation of cyanohydrin ethers is described in the chemical literature [*J. Am. Chem. Soc.*, 93, 5286(1971)].

The alkylated cyanohydrin ether IV is then hydrolyzed to the parent ketone V by sequential treatment with acid and base. For example, a solution IV in tetrahydrofuran is reacted at room temperature with dilute hydrochloric acid. The crude cyanohydrin obtained as a solution by ether extraction is simply washed with dilute sodium hydroxide solution to afford a solution of the ketone V. The pure ketone is isolated and purified by procedures well-known in the art.

The ester group, if desired, may be saponified to afford the free carboxylic acid in the usual way, for example, with potassium hydroxide in aqueous methanol at room temperature. In this case the ketoacid (V, R = H), is obtained.

The ketone V prepared by the above procedure is converted to the furylcarbinol VIII by a reduction process. The most-favored method utilizes a mixture of sodium borohydride and ethanol at a temperature of 20°-35° C. for several hours. The ester or acid V is isolated by any suitable, well-known procedure.

An alternative method for the preparation of V entails treatment of furfural (I) with the Grignard reagent VI [*J. Org. Chem.*, 38, 36(1973)]. This reaction is carried out in the presence of magnesium bromide in an inert solvent, preferably diethyl ether. The 2-substituted-5,6-dihydro-1,3-oxazine derivative VII thus obtained is hydrolyzed with strong base to provide the acid VIII (R = H). The preferred reaction conditions are 2.8 M sodium hydroxide in aqueous ethanol at reflux temperature for several hours.

The conversion of the novel α-(6-carboxyhexyl)furfuryl alcohol derivatives (VIII) to the useful intermediate XI is outlined in Flowsheet B. According to the pathway shown therein, the furylcarbinol VII is treated with an acid catalyst in a mixed aqueous-organic solvent. Representative acid catalysts are formic acid, trichloroacetic acid, dichloroacetic acid, phosphoric acid, and p-toluenesulfonic acid. A preferred acid catalyst is formic acid, at a concentration of about 2N in the solvent, in the presence of 1 to 5 mole % sodium formate. Inert, non-hydroxylic, water-miscible organic solvents such as acetone, dioxane, tetrahydrofuran, and dimethylsulfoxide are used in a suitable proportion with water as solvent for the reaction. A preferred system is 3:2 (V/V) dioxane-water. The optimal temperature for the reaction is in the range 50°-100°.

Acids stronger than the aforementioned catalysts are not as suitable since they augment the formation of by-products.

The product of the first stage of the reaction is the linear enedione (IX) [U.S. Pat. No. 3,952,033]. On occasion this intermediate may be isolated. However, the preferred procedure entails maintenance of the reaction conditions until formation of cyclopentenone (X) is complete.

The substance (X) may be isolated at this stage or used in situ for the next step. In the latter case a strong acid such as sulfuric acid or perchloric acid is added to the solution, and the reaction is run until the equilibrium mixture of X and XI is obtained. This results in formation of more than 90% XI from X. A preferred set of conditions is 2N sulfuric acid in the above solvent, a temperature of 66°, and a reaction time of 20 hours. Under these conditions, the ester group of X, if present, is hydrolyzed to a carboxyl group. The product XI is isolated by well-known procedures.

If the intermediate cyclopentenone X is isolated, the subsequent isomerization to XI may be accomplished by a variety of means. The compound X may be treated with a solution of strong acid such as sulfuric acid or perchloric acid in a mixture of water and an inert, water-miscible, nonhydroxylic organic solvent. The isomerization may also be effected with an aqueous solution of a weak base such as sodium carbonate. Another procedure employs a solution of triethylamine and chloral in an inert solvent such as dichloromethane [*J. Am. Chem. Soc.*, 97, 3258(1975)]. In each case the product XI is isolated by well-known procedures.

FLOWSHEET B

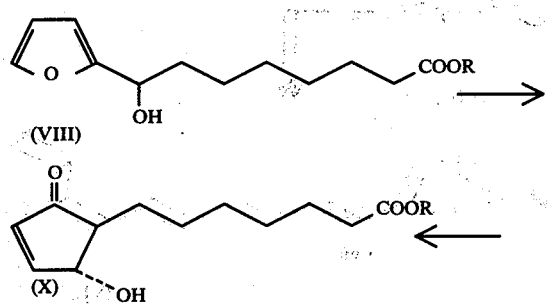
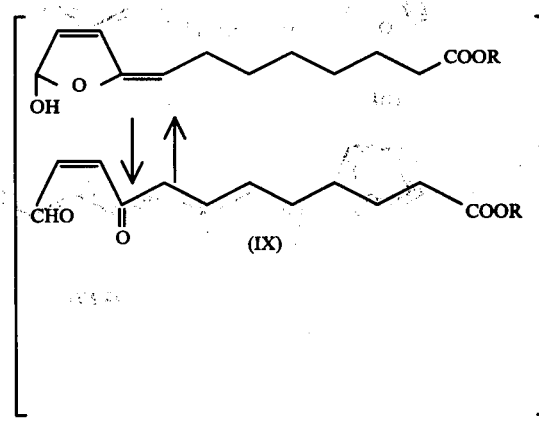

FLOWSHEET B -continued

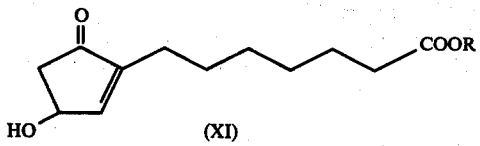

(XI)

The conversion of cyclopentenone XI to prostaglandins is a well-known general method. For the preparation of d,1-prostaglandin E, (d,1-PGE₁) (XIII), the cyclopentenone XI (R = H) is converted to, for example, a bis-tetrahydropyranyl or a bis-trimethylsilyl derivative (XIII) by commonly-used methods. The resulting protected compound is converted to XIII by conjugate addition of a suitable vinyl metal species [see, for example, *Prostaglandins*, 3, 921(1973)]; see Flowsheet C.

For the preparation of 1-PGE₁, methyl ester (XV), the cyclopentenone XI (R = CH₃) is subjected to chemical resolution to afford the (4R) enantiomer [see *Tetrahedron Letters*, 1973, 943]. The tetrahydropyranyl ether XIV has been converted to XV [*J. Am. Chem. Soc.*, 97, 865(1975)]; see Flowsheet C.

treated with 300 mg. of anhydrous sodium carbonate, and the mixture is stirred for 4 hr., diluted with ether, and filtered. The filtrate is concentrated to give a residue which is distilled to give a pale yellow liquid, b.p. 63°–73° C(0.08–0.2 mm).

EXAMPLE 2

Preparation
α-(6-carbethoxyhexyl)-α-(1-ethoxyethoxy)-α-(2-furyl)acetonitrile

To a stirred solution of 84 ml of diisopropylamine in 280 ml of dry tetrahydrofuran (THF) is added 260 ml of 2.3M n-butyllithium in hexane during 30 min. at 0°–5° C. After stirring for 25 min. at −5° C. the solution is cooled to −75° C. and treated with a solution of 113g

FLOWSHEET C

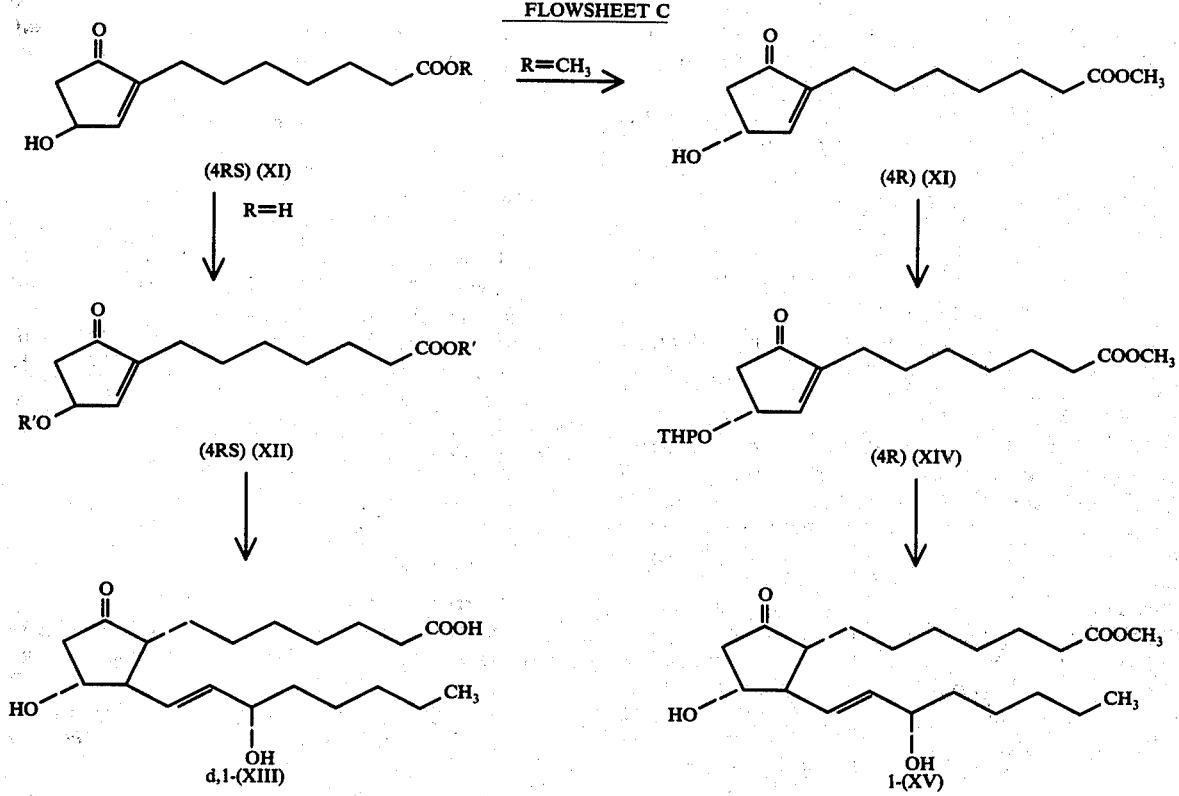

DETAILED DISCLOSURE

EXAMPLE 1

Preparation of 1-Ethoxyethyl ether of Furfural Cyanohydrin

To a stirred sample of 10.0g (81.2 mmol) of furfural cyanohydrin [*Chem. Ber.*, 87, 276(1954)] is added 9.1g (127 mmol) of ethyl vinyl ether dropwise during a 30 min. period at 22°–38° C. During the addition 2 or 3 drops of dichloroacetic acid are added as catalyst. After 3 hr. an additional drop of the catalyst is added. After 20 hr. at ambient temperature the reaction mixture is (0.58 mol) of 1-ethoxyethyl ether of furfural cyanohydrin (Example 1) in 115 ml of hexamethylphosphoric triamide during 45 min. at −75° to −65° C. After stirring for 25 min. at −75° C. the solution is treated with 136g (0.576 mol) of ethyl 7-bromoheptanoate during 40 min. −75° to −65° C. After slow addition of 280 ml of TMF as rinse the mixture is stirred at −75° C. for 2.5 hr. and at ambient temperature for 18 hr. The reaction mixture is partitioned with water and ether. The ether phase is washed with brine, dried over sodium sulfate, filtered through Celite, and concentrated.

The residue is dissolved in 500 ml of 1:1 hexanebenzene, and the solution is filtered through a pad of 300g of silica gel. The pad is washed with 2 l of the same solvent. The filtrate is concentrated to give 185g of oil.

EXAMPLE 3

Preparation of Ethyl 7-(2-furoyl)heptanoate

To a stirred solution of 185g of α-(6-carbethoxyhexyl)-α-(1-ethoxyethoxy)-α-(2-furyl)acetonitrile (Example 2) in 1600 ml of THF is added 580 ml of 2N hydrochloric acid. The resulting solution is stirred at room temperature for 3.5 hr., and extracted several times with ether. The extract is washed successively with 5% hydrochloric acid, brine, 0.5N sodium hydroxide, and brine; dried over sodium sulfate; and concentrated under high vacuum to give 125g of oil. The crude product is distilled to give 88g of light yellow liquid, b.p. 150° C (0.05 mm).

EXAMPLE 4

Preparation of α-(6-Carbethoxyhexyl) furfuryl alcohol

To a stirred solution of 85g (0.337 mol) of ethyl 7-(2-furoyl)heptanoate (Example 3) in 500 ml of abs. ethanol is added 12.75g (0.337 mol) of sodium borohydride in small portions during 20 min. at 20°-35° C. The mixture is stirred at ambient temperature for 3.5 hr., poured into 2.5 l of water, and extracted with ether. The extract is washed with brine, dried over magnesium sulfate, and concentrated to give a pale yellow oil (85.8g).

EXAMPLE 5

Preparation 2-[7-(2-furyl)-7-hydroxyheptyl]-4,4,6-trimethyl-5,6-dihydro-1,3-oxazine To a stirred suspension of 0.61g (25 mg. atom) of magnesium in 30 ml of ether is added 1.76g (11 mmol) of bromine dropwise during 20 min. at 15°-20° C. After 15 min. the mixture is treated dropwise with a solution of 2.90g (10 mmol) of 2-(6-bromohexyl)-4,4,6-trimethyl-5,6-dihydro-1,3-oxazine [J. Org. Chem., 38, 36(1973)] in 5 ml of ether. The resulting mixture is stirred at ambient temperature for 3 hr. and at reflux temperature for 30 min. The mixture is cooled to 0° and treated during 20 min. with a solution of 1.15g (12 mmol) of furfural. The stirred mixture is brought to reflux temperature during 20 min., maintained at that temperature for 20 min., cooled and treated with 2.5 ml of saturated ammonium chloride. The mixture is diluted with ether and water and filtered. The organic phase is separated, washed with brine, dried over potassium carbonate, and concentrated.

The residue is subjected to dry column chromatography on silica gel with 1% acetic acid in ethyl acetate as developing solvent to give a light yellow oil.

EXAMPLE 6

Preparation of α-(6-carboxyhexyl)furfuryl alcohol

Method A. To a stirred solution of 82.8g of α-(6-carbethoxyhexyl)furfuryl alcohol (Example 4) in 800 ml of methanol is added a solution of 64.5g of 85% potassium hydroxide in 100 ml of water and 200 ml of methanol during 10 min. The resulting solution is stirred at ambient temperature for 18 hr., concentrated to remove methanol, diluted with water, and extracted with ether. The aqueous phase is acidified with cooling to pH = 5.5 with 4N hydrochloric acid, saturated with salt, and extracted with ether. The extract is washed with brine, dried over magnesium sulfate, and concentrated to give 74.3g of amber oil.

Method B. A stirred mixture of 230 mg (0.75 mmol) of 2-[7-(2-furyl)-7-hydroxyheptyl]-4,4,6-trimethyl-5,6-dihydro-1,3-oxazine (Example 5), 3.75 ml of 3N sodium hydroxide, and 1.25 ml of ethanol is heated at reflux for 16 hr. The solution is diluted with brine and extracted with ether. The aqueous phase is acidified to pH = 2 and extracted with ethyl acetate. The extract was washed with brine, dried over magnesium sulfate, and concentrated.

EXAMPLE 7

Preparation of 2-(6-carboxyhexyl)-3-hydroxycyclopent-4-en-1-one.

A stirred mixture of 65.0g (0.287 mol) of α-(6-carboxyhexyl)furfuryl alcohol (Example 6), 113 ml of 97% formic acid, 4.95g of sodium formate, 100 mg of hydroquinone, and 1430 ml of 3:2 dioxane-water is heated at reflux temperature for 19 hr. The solution is concentrated to volume of about 750 ml, diluted with water, saturated with salt, and extracted with ether. The extract is washed with brine, dried over magnesium sulfate, and evaporated with toluene chaser to give an amber solid.

EXAMPLE 8

Preparation of 2-(6-Carbethoxyhexyl)-3-hydroxycyclopent-4-en-1-one.

A stirred mixture of 2.0g (7.87 mmol) of α-(6-carbethoxyhexyl)furfuryl alcohol (Example 4), 5.93 ml of 97% formic acid, 268 mg of sodium formate, 10 mg of hydroquinone, and 40 ml of 3:2 dioxane-water is stirred at reflux for 18 hr. The solution is cooled, saturated with salt, and extracted with ether. The extract is washed with brine, dried over magnesium sulfate, and concentrated to give an amber oil.

EXAMPLE 9

Preparation of 2-(6-carboxyhexyl-4-hydroxycyclopent-2-en-1-one

To a stirred solution of 67.2g of 2-(6-carboxyhexyl)-3-hydroxycyclopent-4-en-1-one (Example 7) in 1430 ml of 3:2 dioxane-water is added 76 ml of sulfuric acid (sp. gr. = 1.84) during 45 min. The solution is stirred at 66° C. for 20 hr., cooled, saturated with salt, and extracted with ether. The extract is washed with brine, dried over magnesium sulfate, and concentrated.

The residue is subjected to chromatography on silica gel with chloroform progressively enriched in ether to afford 32.7g of oil.

I claim:

1. A compound of the formula:

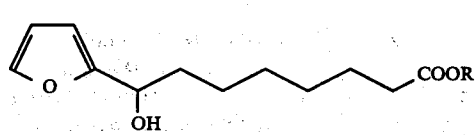

wherein R is selected from the group consisting of hydrogen and $C_1-C_6$ alkyl.

2. The compound according to claim 1, α-(6-carboxyhexyl) furfuryl alcohol.

3. The compound according to claim 1, α-(6-carbomethoxyhexyl) furfuryl alcohol.

4. The compound according to claim 1, α-(6-carbethoxyhexyl) furfuryl alcohol.

5. The compound according to claim 1, α-(6-carbohexoxyhexyl) furfuryl alcohol.

* * * * *